(12) United States Patent
Hokii et al.

(10) Patent No.: US 9,949,896 B2
(45) Date of Patent: Apr. 24, 2018

(54) FILLER FOR DENTAL GLASS IONOMER CEMENT AND METHOD FOR MANUFACTURING THE SAME

(71) Applicant: GC CORPORATION, Tokyo (JP)

(72) Inventors: Yusuke Hokii, Tokyo (JP); Ryosuke Yoshimitsu, Tokyo (JP); Futoshi Fusejima, Tokyo (JP)

(73) Assignee: GC CORPORATION, Tokyo (JP)

( * ) Notice: Subject to any disclaimer, the term of this patent is extended or adjusted under 35 U.S.C. 154(b) by 0 days.

(21) Appl. No.: 15/110,293

(22) PCT Filed: Jan. 30, 2015

(86) PCT No.: PCT/JP2015/052668
§ 371 (c)(1),
(2) Date: Jul. 7, 2016

(87) PCT Pub. No.: WO2015/115597
PCT Pub. Date: Aug. 6, 2015

(65) Prior Publication Data
US 2016/0324729 A1    Nov. 10, 2016

(30) Foreign Application Priority Data
Jan. 31, 2014   (JP) .................................. 2014-018077

(51) Int. Cl.
| | |
|---|---|
| *A61K 6/08* | (2006.01) |
| *A61F 2/00* | (2006.01) |
| *C08G 61/04* | (2006.01) |
| *A61K 6/00* | (2006.01) |
| *A61K 6/083* | (2006.01) |
| *A61Q 11/00* | (2006.01) |

(52) U.S. Cl.
CPC .......... *A61K 6/0088* (2013.01); *A61K 6/0835* (2013.01); *A61Q 11/00* (2013.01)

(58) Field of Classification Search
CPC ...... A61K 6/088; A61K 6/0835; A61Q 11/00; C08L 33/10
USPC ................. 523/116, 115, 113, 105, 1; 520/1
See application file for complete search history.

(56) References Cited

U.S. PATENT DOCUMENTS

| | | | |
|---|---|---|---|
| 5,332,429 A | 7/1994 | Mitra et al. | |
| 6,214,101 B1 | 4/2001 | Nakaseko | |
| 6,355,585 B1* | 3/2002 | Suzuki | A61K 6/0017 106/35 |
| 2009/0012209 A1* | 1/2009 | Eckhardt | A61K 6/0017 523/116 |
| 2009/0030110 A1 | 1/2009 | Klee et al. | |
| 2013/0178552 A1 | 7/2013 | Kruber et al. | |
| 2017/0007506 A1* | 1/2017 | Hokii | A61K 6/0835 |

FOREIGN PATENT DOCUMENTS

| | | |
|---|---|---|
| JP | 06-508337 A | 9/1994 |
| JP | 11-228327 A | 8/1999 |
| JP | 2008-500292 A | 1/2008 |
| JP | 2009-503002 A | 1/2009 |
| JP | 2013-531019 A | 8/2013 |

OTHER PUBLICATIONS

Alireza Moshaverinia, et al; "Click Chemistry: A Potential Platform for Development of Novel Dental Restorative Materials", Journal of Macromolecular Science, Part A: Pure and Applied Chemistry; vol. 49, No. 4-6, pp. 288-292; Published online Mar. 23, 2012.
International Search Report dated Apr. 14, 2015; PCT/JP2015/052668.

* cited by examiner

*Primary Examiner* — Jessica Whiteley
(74) *Attorney, Agent, or Firm* — Ladas & Parry LLP

(57) ABSTRACT

Provided is a filler for dental glass ionomer cements, the filler to a surface of which a compound(s) having a carboxyl group(s) is/are bound via a silicon atom, for the purpose of providing: a filler suitable for dental glass ionomer cements that can provide a hardened cement having a high strength by being mixed with a dental glass ionomer cement composition, the filler that can be easily manufactured from a general inorganic powder as a raw material; and a manufacturing method of the filler for dental glass ionomer cements. The manufacturing method includes binding a carboxylic acid having an unsaturated double bond(s) exclusive of a (meth)acrylate compound to an inorganic powder whose surface is treated with a silane coupling agent having an unsaturated double bond(s).

8 Claims, No Drawings

FILLER FOR DENTAL GLASS IONOMER CEMENT AND METHOD FOR MANUFACTURING THE SAME

TECHNICAL FIELD

The present invention relates to fillers suitable for dental glass ionomer cements and methods for manufacturing the fillers.

BACKGROUND ART

In using dental glass ionomer cements, α-β unsaturated carboxylic acid polymers such as polycarboxylic acid, and fluoroaluminosilicate glass powders are allowed to react to each other to be hardened, in the presence of water. These dental glass ionomer cements are widely used in dentistry, because they have excellent characteristics, for example very good biocompatibility, excellent aesthetic property of semi-transparent hardened body, excellent adhesion to tooth substrates such as enamel and dentine, and an anticariogenic effect by fluoride contained in glass.

A general dental glass ionomer cement is formed from a powder component and a liquid component, and therefore has a demerit that its handling such as measuring and mixing are troublesome. The applicant of the present invention previously developed a glass ionomer cement composition in a paste form consisting of a first paste whose main components are an α-β unsaturated carboxylic acid polymer, water, and a filler that does not react with the α-β unsaturated carboxylic acid polymer, and a second paste whose main components are a fluoroaluminosilicate glass powder and a polymerizable monomer not having an acid group, wherein a polymerization initiator is mixed with at least either one of the pastes, depending on the polymerization method of the polymerizable monomer (see Patent Literature 1 for example).

However, the strength of a hardened body of the dental glass ionomer cement composition is insufficient. This is because the interaction between the filler that does not react with the α-β unsaturated carboxylic acid polymer and the base component of the cement (the α-β unsaturated carboxylic acid polymer and fluoroaluminosilicate glass) is weak.

Against this problem, a filler for dental materials including: a particle of feldspar or feldspar derivative coated by a silicon compound containing a reactive group; and a polymerizable resin that can react with the reactive group is disclosed (see Patent Literature 2 for example). However, the strength of a hardened body of this filler is insufficient, because the interaction of the filling material with main components of cement is weak. In addition, feldspar is a natural product, whose composition is inhomogeneous, and metal contained in feldspar easily elutes in the presence of water. As such, feldspar is not a suitable filling material for glass ionomer cements.

In order to solve this problem, suggested is a filler whose surface is treated with a polyacid selected from the group consisting of homopolymers and copolymers of acrylic acid, maleic acid, itaconic acid, methacrylic acid, and combinations thereof, and with aminoalkyltrialkoxysilane as a linking group (see Patent Literature 3 for example). However, this surface treatment tends to be troublesome and cost a lot, and has a problem that the surface easily gets uneven and a stable effect is difficult to be obtained.

CITATION LIST

Patent literatures

Patent Literature 1: JP H11-228327 A
Patent Literature 2: JP 2013-531019 A
Patent Literature 3: JP 2009-503002 A

SUMMARY OF INVENTION

Technical Problem

An object of the present invention is to provide a filler suitable for dental glass ionomer cements, the filler which can provide a hardened cement having a high strength when the filler is mixed with a dental glass ionomer cement composition, and which can be easily manufactured from a general inorganic powder as a raw material, and a manufacturing method of the filler.

Solution to Problem

As a result of intensive researches for solving the above problems, the inventors of the present invention found that it is possible to easily manufacture a filler for dental glass ionomer cements, the filler to a surface of which a compound(s) having a carboxyl group(s) is/are bound via a silicon atom. The inventors also found that it is possible, with the filler, to obtain a hardened cement having a high strength, because the compound having a carboxyl group(s) is bound to a surface of a general inorganic powder via a silicon atom, and when the filler is mixed with a dental glass ionomer cement composition, the carboxyl group interacts with the main component of the cement via metal ions, whereby the filler stabilizes in the composition. The present invention has been completed based on the above findings.

That is, the present invention is a filler for dental glass ionomer cements, the filler to a surface of which a compound (s) having a carboxyl group (s) is/are bound via a silicon atom.

Another embodiment of the present invention is a method for manufacturing a filler for dental glass ionomer cements including: binding a carboxylic acid having an unsaturated double bond(s) exclusive of a (meth)acrylate compound, to an inorganic powder whose surface is treated with a silane coupling agent having an unsaturated double bond(s).

Another embodiment is a filler for dental glass ionomer cements manufactured by the method for manufacturing a filler for dental glass ionomer cements, the method including: binding a carboxylic acid having an unsaturated double bond(s) exclusive of a (meth)acrylate compound, to an inorganic powder whose surface is treated with a silane coupling agent having an unsaturated double bond(s).

Advantageous Effects of Invention

The filler for dental glass ionomer cements according to the present invention is a filler that can be easily manufactured from an inorganic powder and a carboxylic acid having an unsaturated double bond(s) exclusive of a (meth)acrylate compound as raw materials. It is possible to obtain a hardened cement having a high strength by mixing the filler with a dental glass ionomer cement composition.

DESCRIPTION OF EMBODIMENTS

Hereinafter the embodiments of the present invention will be described in detail.

The filler for dental glass ionomer cements according to the present invention is a filler for dental glass ionomer cements, the filler to a surface of which a compound(s) having a carboxyl group(s) is/are bound via a silicon atom.

A compound having a carboxyl group(s) is bound to a surface of this filler for dental glass ionomer cements, via a silicon atom. The carboxyl group interacts with the base component of cement via metal ions, and the filler stabilizes in the composition. Therefore, the filler, which can provide a hardened cement having a high strength, is suitable for dental glass ionomer cements.

The filler for dental glass ionomer cements is manufactured by binding:
(a) an inorganic powder whose surface is treated with a silane coupling agent having an unsaturated double bond(s); and
(b) a carboxylic acid having an unsaturated double bond(s) exclusive of a (meth)acrylate compound.

Examples of the inorganic powder (a) include: colloidal silica which does not react with acids in the presence of water; silica powders such as crystalline silica; silica sand which is a mineral; quarts; crystalline glasses that do not emit metal ions, such as strontium glass, barium glass, and borosilicate glass; fluoroaluminosilicate glass which has a reactivity with acids in the presence of water; alumina powders; titanium oxide powders; and barium sulfate. If water is not used for a dispersion medium, a mixture of two or more kinds of these inorganic powders can be used. If water is used for a dispersion medium, a mixture of two or more kinds of the inorganic powders each having the same reactivity with water can be used. Among them, one or two or more kinds selected from the group consisting of silica powders, quarts, alumina powders, titanium oxide powders, and fluorialuminosilicate glass are preferable.

The average particle size of the inorganic powder (a) is preferably in the range of from 0.02 to 10 µm. If the average particle size is more than 10 µm, the surface smoothness of the cement after hardened is not obtained, therefore the contact feeling in oral cavities gets worse. On the other hand, if a fine powder of less than 0.02 µm in average particle size is used, it gets difficult to mix an absolute quantity of the inorganic powder in the composition, therefore the physical properties of the hardened cement tends to degrade.

The surface of the inorganic powder (a) needs to be treated with a silane coupling agent having an unsaturated double bond(s). Examples of the silane coupling agent having an unsaturated double bond(s) used for the surface treatment include vinyl-based silane coupling agents such as vinyltrimethoxysilane, vinyltriethoxysilane, γ-methacryloxypropyltrimethoxysilane, γ-methacryloxypropylmethyldimethoxysilane, vinyltrichlorosilane, and vinyltris(2-methoxyethoxy)silane. This treatment chemically fixes the silane coupling agent having an unsaturated double bond(s) on the surface of the inorganic powder. A carbon atom on the unsaturated double bond binds with a carbon atom on the unsaturated double bond of the carboxylic acid having an unsaturated double bond(s) exclusive of a (meth)acrylate compound which is described later.

The used amount of the silane coupling agent is, to 100 pts. mass of the inorganic powder, preferably in the range of from 0.01 to 20 pts. mass. If the amount is less than 0.01 pts. mass, a sufficient strength does not tend to be obtained, and if the amount is more than 20 pts. mass, a homogenous treatment powder does not tend to be obtained.

The blending amount of the inorganic powder (a) whose surface is treated with a silane coupling agent having an unsaturated double bond(s) is preferably in the range of from 20 to 80 mass % to the total amount of (a) to (c). If the amount is less than 20 mass %, the effect is difficult to be obtained, and if the amount is more than 80 mass %, the preparation itself of the reaction liquid tends to be difficult.

Regarding the carboxylic acid (b) having an unsaturated double bond(s) exclusive of a (meth)acrylate compound, a carbon atom on the unsaturated double bond binds with a carbon atom on the unsaturated double bond of the silane coupling agent bound to the surface of the inorganic powder described above. This eventually introduces the carboxyl group to the surface of the filler for dental glass ionomer cements via a silicon atom, and the strength of the filler for dental glass ionomer cements itself improves. Examples of the carboxylic acid having an unsaturated double bond(s) exclusive of a (meth)acrylate compound include acrylic acid, methacrylic acid, itaconic acid, fumaric acid, maleic acid, aconitic acid, angelic acid, citraconic acid, crotonic acid, glutaconic acid, metaconic acid, mesaconic acid, muconic acid, tiglic acid, cinnamic acid, allylmalonic acid, butenoic acid, pentenoic acid, hexenoic acid, octenoic acid, nonenoic acid, decenoic acid, oleic acid, linoleic acid, and linolenic acid. The acid anhydrides thereof, structural isomers thereof, and cis-trans isomers thereof are also included in the examples. These carboxylic acids can be used alone, and a mixture of two or more kinds thereof can also be used. Among them, acrylic acid, itaconic acid, and maleic acid are especially preferable, because they have beneficial effects on improving the strength of the hardened cement. "exclusive of a (meth)acrylate compound" means that the carboxylic acid does not have the partial structure shown by the following chemical formula (X is a hydrogen atom or methyl group, and the structure beyond the dashed line can be in any form).

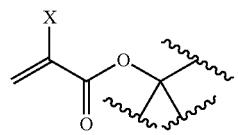

[Formula 1]

The filler for dental glass ionomer cements according to the present invention is manufactured by binding (a) an inorganic powder whose surface is treated with a silane coupling agent having an unsaturated double bond(s) and (b) a carboxylic acid having an unsaturated double bond(s) exclusive of a (meth)acrylate compound, at the carbon atoms of their unsaturated double bonds.

In the present invention, the step of binding the above inorganic powder (a) and the carboxylic acid (b) is carried out by a liquid-phase polymerization or emulsion polymerization. That is, the inorganic powder (a), the carboxylic acid (b), and an adequate polymerization initiator are allowed to react in a suitable dispersion medium. According to this method, the inorganic powder (a) and the carboxylic acid (b) can be uniformly bound to each other with a high density, because the inorganic powder (a) is dispersed in a dispersion medium. Therefore it is possible to obtain a homogeneous and effective filler for dental glass ionomer cements. This method also has an advantage of easy manufacturing of the filler, because the filler can be purified only by a removal of the dispersion medium after the polymerization.

In contrast, a solid-phase polymerization which is a conventional and general making method of an organic-inorganic composite filler does not have the above-described advantage, and a homogeneous and effective filler for dental glass ionomer cements is difficult to be obtained with the solid-phase polymerization. In addition, with the solid-phase polymerization, a grinding and particle size adjustment are needed after the polymerization, which causes the manufacturing cost to increase. Therefore, the solid-phase polymerization is not applied in the present invention.

The blending amount of the carboxylic acid (b) having an unsaturated double bond(s) exclusive of a (meth)acrylate compound is preferably in the range of from 20 to 80 mass % to the total amount of (a) to (c). If the amount is less than 20 mass %, the effect is difficult to be obtained, and if the amount is more than 80 mass %, the preparation itself of the reaction liquid tends to be difficult.

The polymerization initiator (c) has a function to bind the carboxylic acid (b) having an unsaturated double bond(s) exclusive of a (meth)acrylate compound to the inorganic powder (a) treated with a silane coupling agent having an unsaturated double bond(s), between their unsaturated double bonds, via a carbon-carbon single bond. As the polymerization initiator, polymerization initiator used for conventional dental materials can be used without particular limitations, and an effective method for polymerization reaction system can be adequately chosen depending on the kind and combination of the polymerization initiator. Specifically, thermal polymerization initiators are preferable for the purpose of securing the polymerization. As the thermal polymerization initiators, organic metal compounds such as azobisisobutyronitrile as an azo compound and tributyl borate are preferable. Diacyl peroxides having aromatic series, and peroxy esters which are regarded as esters of perbenzoic acids, such as benzoyl peroxide, 2,4-dichlorobenzoylperoxide, m-tolyl peroxide, t-butyl peroxybenzoate, di-t-butylperoxyisophthalate, 2,5-dimethyl-2,5-di(benzoylperoxy)hexane, and 2,5-dimethyl-2,5-di[(o-benzoyl)benzoylperoxy] hexane can also be used. As a water-soluble polymerization catalyst, persulfates such as potassium peroxodisulfate, sodium peroxodisulfate, ammonium persulfate, potassium persulfate, sodium persulfate, potassium peroxydiphosphate, and potassium peroxydisulfate are also preferable. A mixture of one or two or more kinds of these thermal polymerization initiator can also be used. If a polymerization initiator which is insoluble in alcohol, such as potassium peroxodisulfate, is used, a dispersion medium in which the polymerization initiator can dissolve needs to be used.

The blending amount of the polymerization initiator (c) is preferably in the range of from 0.1 to 3 mass % to the total amount of (a) to (c). If the amount is less than 0.1 mass %, it is difficult to obtain a sufficient polymerization effect. On the other hand, though depending on the kind and blending ratio of the unsaturated carboxylic acid to be used, if the amount is more than 3 mass %, the length of the polymer chain to be obtained gets short, and a sufficient effect on improvement in the physical property of the cement does not tend to be obtained.

As the dispersion medium (d), preferably used is a medium which sufficiently disperses the inorganic powder treated with a silane coupling agent having an unsaturated double bond(s), and which sufficiently dissolves both the carboxylic acid (b) having an unsaturated double bond(s) exclusive of a (meth)acrylate compound and the polymerization initiator (c). A mixture solvent of water and alcohol is especially preferably used. In specific, the alcohol concentration in the mixture solvent is preferably in the range of from 30 to 80%. If the concentration is more than 80%, the solubility of the water-soluble polymerization initiator tends to degrade, whereby the reaction efficiency tends to degrade.

If the concentration is less than 30%, the dispersion efficiency of the inorganic powder (a) treated with a silane coupling agent having an unsaturated double bond(s) tends to degrade.

If an inorganic powder having a reactivity with acids is used as the inorganic powder (a), it is necessary to select a non-aqueous dispersion medium as the dispersion medium (d), in order to prevent the progression of acid-base reaction in the polymerization reaction. Considering the solubility of the carboxylic acid (b) having an unsaturated double bond(s) exclusive of a (meth)acrylate compound, a lower alcohol is preferably used, and ethanol is especially preferably used. It is preferable to carry out a dehydration treatment on the dispersion medium by molecular sieves, before the medium is used.

By a polymerization reaction of a mixture including the above (a) to (c), the carboxylic acid (b) having an unsaturated double bond(s) chemically binds to the inorganic powder (a) treated with a silane coupling agent having an unsaturated double bond(s), via a silicon atom. That is, a carbon atom on the unsaturated double bond in an extension of the silicon atom of the inorganic powder (a) treated with a silane coupling agent having an unsaturated double bond(s) and a carbon atom on the unsaturated double bond of the carboxylic acid (b) having an unsaturated double bond(s) chemically bind to each other. This makes it possible to obtain a filler for dental glass ionomer cements in which a compound(s) having a carboxyl group(s) is/are bound to a surface of an inorganic powder via a silicon atom. An effective method for polymerization reaction system can be adequately chosen depending on the kind and combination of the polymerization medium.

According to the method for manufacturing a filler for dental glass ionomer cements of the present invention, the filler for dental glass ionomer cements can be made by mixing and polymerizing (a) an inorganic powder treated with a silane coupling agent having an unsaturated double bond(s), (b) a carboxylic acid having an unsaturated double bond(s) exclusive of a (meth)acrylate compound, and (c) a polymerization catalyst, in (d) a dispersion medium. Therefore, the filler can be very easily made by the method. In addition, different fillers having different properties can be manufactured by the method, because the carboxylic acid (d) having an unsaturated double bond(s) exclusive of a (meth)acrylate compound can be selected from many kinds of carboxylic acids.

It is needless to say that a photopolymerization initiator, antibacterial agent, colorant, stabilizer, and the like which are normally used as needed can be adequately blended with the filler for dental glass ionomer cements according to the present invention.

Hereinafter the filler for dental glass ionomer cements according to the present invention and the manufacturing method thereof will be described with specific examples. However, the present invention is not limited to these Examples.

EXAMPLES

<<Preparation of Filler for Dental Glass Ionomer Cement>>

Example 1

γ-methacryloxypropyltrimethoxysilane in an amount of 20 pts. mass diluted with ethanol to be 50 mass % was added to 100 pts. mass of quartz powder whose average particle size was 1.8 μm, and mixed by an automatic grinding machine. The obtained inorganic powder was subjected to a heat treatment at 110° C. for 2 hours. The obtained treated powder was determined as a quartz powder 10% silane-treated inorganic powder.

Next, a mixed liquid of water:ethanol=2:1 was prepared to be (d) a dispersion medium. The silane-treated inorganic powder in an amount of 45.3 mass % and itaconic acid in an amount of 53.5 mass %, to the total amount of (a) to (c), were put in a reaction container, and thereafter diluted in a measuring cylinder by the mixed liquid so that the resultant liquid was 100 mL.

The resultant liquid was stirred at 60° C. for 30 minutes. After that, 1.2 mass % of potassium peroxodisulfate was put in the liquid, and polymerized for 1 hour. A centrifugal separation was carried out to the obtained liquid to remove supernatant. Thereafter, the obtained material was suspended again in water. This operation was repeated for four times, to remove unreacted itaconic acid and polymerization initiator. Further, moisture was removed from the obtained material by a freeze dryer, whereby a filler for dental glass ionomer cements which was white and in a bulky powder form was obtained.

Examples 2 to 5

A filler for dental glass ionomer cements was prepared in the same way as in Example 1.

Examples 6 to 8

A filler was prepared in the same way as in Example 1, except that azobisisobutyronitrile was used as the polymerization initiator (c), and ethanol to which a dehydration treatment was carried out with molecular sieves was used as the dispersion medium (d).

Comparative Example

In Comparative Example 1, the quartz powder 10% silane-treated powder was used as it was.

Comparative Example 2

A filler was prepared in the same way as in Example 1, except that the polymerization initiator (c) was not contained in the filler.

Comparative Example 3

A filler was prepared in the same way as in Example 1, except that potassium peroxodisulfate was used as the polymerization initiator (c), and ethanol to which a dehydration treatment was carried out with molecular sieves was used as the dispersion medium (d). Table 1 collectively shows each blending amount described above and average particle sizes of the obtained fillers for glass ionomer cements.

TABLE 1

| | | Example 1 | Example 2 | Example 3 | Example 4 | Example 5 | Example 6 | Example 7 | Example 8 | Comparative Example 1 | Comparative Example 2 | Comparative Example 3 |
|---|---|---|---|---|---|---|---|---|---|---|---|---|
| (a) Inorganic powder whose surface is treated with silane treatment agent having unsaturated double bond | Quartz powder 10% silane-treated powder | 45.3 | 45.3 | 45.3 | 45.3 | 45.3 | | | | 100.0 | 45.8 | 45.3 |
| | Fluoroaluminosilicate glass powder A 2% silane-treated powder | | | | | | 56.9 | 60.3 | | | | |
| | Fluoroaluminosilicate glass powder B 2% silane-treated powder | | | | | | | | 60.3 | | | |
| (b) Carboxylic acid having unsaturated double bond exclusive of (meth)acrylate compound | Itaconic acid | 53.5 | 53.5 | 53.5 | 44.4 | 44.4 | 42.6 | 30.2 | 30.2 | | 54.2 | 53.5 |
| | Acrylic acid | | | | 9.1 | | | 9.0 | | | | |
| | Maleic acid | | | | | 9.1 | | | 9.0 | | | |
| (c) Polymerization initiator | Potassium peroxodisulfate | 1.2 | 1.2 | 1.2 | 1.2 | 1.2 | | | | | | 1.2 |
| | Azobisisobutyronitrile | | | | | | 0.5 | 0.5 | 0.5 | | | |
| (d) dispersion medium (water:ethanol) | | 2:1 | 2:1 | 2:1 | 2:1 | 2:1 | ethanol only | ethanol only | ethanol only | | 2:1 | ethanol only |
| Reaction condition | | 60° C. 1 hour | 60° C. 3 hours | 60° C. 6 hours | 60° C. 6 hours | 60° C. 6 hours | 60° C. 6 hours | 60° C. 6 hours | 60° C. 6 hours | | 60° C. 3 hours | 60° C. 6 hours |
| Average particle size (μm) | | 1.8 | 1.8 | 1.8 | 1.8 | 1.8 | 2.4 | 2.4 | 2.4 | 1.8 | 1.8 | 1.8 |
| Zeta potential (mV) | | −19 | −35 | −38 | −43 | −35 | −41 | −40 | −38 | −16 | −14 | −14 |

<<Preparation of Fluoroaluminosilicate Glass Powder>>
<Fluoroaluminosilicate Glass Powder A>

By a mortar, 22 g of aluminum oxide, 23 g of silica, 12 g of calcium fluoride, 15 g of calcium phosphate, and 28 g of strontium fluoride were sufficiently mixed and stirred. The obtained batch was put in a porcelain crucible, and heated to 1200° C. at approximately 7° C./min of temperature rising rate in an electric furnace, and kept at 1200° C. for 3 hours. The obtained melt was poured into water, whereby a quenched glass was obtained. The quenched glass was pulverized to be a fluoroaluminosilicate glass powder A. The average particle size of this inorganic powder was 2.5 µm.

<Fluoroaluminosilicate Glass Powder B>

By a mortar, 23 g of aluminum oxide, 31 g of silica, 1 g of calcium fluoride, 9 g of cryolite, 2 g of aluminum phosphate, and 34 g of strontium fluoride were sufficiently mixed and stirred. The obtained batch was put in a porcelain crucible, and heated to 1200° C. at approximately 7° C./min of temperature rising rate in an electric furnace, and kept at 1200° C. for 3 hours. The obtained melt was poured into water, whereby a quenched glass was obtained. The quenched glass was pulverized to be a fluoroaluminosilicate glass powder B. The average particle size of this inorganic powder was 2.5 µm.

<<Evaluation of Filler by Zeta Electrometer>>

The obtained filler was suspended in 10 mM Nacl-0.01% TritonX-100 solution, so that the amount of the filler was 0.1 mass % in the solution. The resultant mixture was irradiated with ultrasonic waves for 10 minutes, whereby the filler was sufficiently dispersed. This mixture was used as a measurement specimen. The variation of electric charge on the surface of the specimen was measured by a zeta electrometer (ELS-Z, manufactured by OTSUKA ELECTRONICS CO., LTD.). The bonding amount of carboxyl groups was relatively larger as the value of the zeta potential was negative and its absolute value was larger. The results are together shown in Table 1.

<<Making of Powder-liquid Type Dental Glass Ionomer Cement Composition>>

Each component was mixed at the blending amount shown in Table 2, whereby powder components and liquid components of powder-liquid type dental glass ionomer cement compositions were prepared.

<<Bending Strength Test>>

Each powder component and liquid component prepared as above was scaled at the powder-liquid ratio shown in Table 2. The scaled components were kneaded for 30 seconds on a kneading paper by a spatula. A metal split mold of 2 mm in width, 2 mm in height, and 25 mm in length was filled with the obtained kneaded material. The bottom and top of the mold were covered up by metal plates. With a clamp, the kneaded material with the mold was welded by pressure and fixed. The obtained material was left in an atmosphere at a temperature of 37° C. and at a humidity of 100% for 1 hour to be cured. After that, the metal split mold was removed from the material. The obtained stick-shaped specimen was immersed in 37° C. of distilled water for 24 hours. Thereafter, the specimen was subjected to a compression test under a condition of 1 mm/min of crosshead speed, by a universal testing machine (Autograph, manufactured by Shimadzu Corporation). In each of the compositions 1 to 8, any one of the fillers for dental glass ionomer cements according to Examples 1 to 6 was blended, and in each of the compositions 9 to 11, any one of the fillers according to Comparative Examples 1 to 3 was blended. The results are together shown in Table 2.

TABLE 2

| | | | Compositions with fillers of Examples | | | | | | | | Compositions with fillers of Comparative Examples | | |
|---|---|---|---|---|---|---|---|---|---|---|---|---|---|
| | | | Composition 1 | Composition 2 | Composition 3 | Composition 4 | Composition 5 | Composition 6 | Composition 7 | Composition 8 | Composition 9 | Composition 10 | Composition 11 |
| Powder component | Fluoroaluminosilicate glass powder | Fluoroaluminosilicate glass powder A | 94 | 94 | 94 | 94 | 94 | 94 | | | 94 | | |
| | | Fluoroaluminosilicate glass powder B | | | | | | | 95 | 95 | | 95 | 95 |
| | α-β unsaturated carboxylic acid polymer | Polyacrylic acid | 4 | 4 | 4 | 4 | 4 | 4 | 5 | 5 | 4 | 5 | 5 |
| | Filler for dental ionomer cement composition | Example 1 | 5 | | | | | | | | | | |
| | | Example 2 | | 5 | | | | | | | | | |
| | | Example 3 | | | 1 | 2.5 | 5 | | | | | | |
| | | Example 6 | | | | | | 5 | | | | | |
| | Other filler | Comparative Example 1 | | | | | | | | | 5 | | |
| Liquid component | α-β unsaturated carboxylic acid polymer | Polyacrylic acid | 45 | 45 | 45 | 45 | 45 | 45 | 43 | 43 | 43 | 43 | 43 |
| | Water | | 50 | 50 | 50 | 50 | 50 | 50 | 45 | 45 | 50 | 45 | 45 |
| | Filler for dental ionomer cement composition | Example 4 | | | | | | | 5 | | | | |
| | | Example 5 | | | | | | | | 5 | | | |
| | Other filler | Comparative Example 2 | | | | | | | | | | 5 | |
| | | Comparative Example 3 | | | | | | | | | | | 5 |
| | Acid (for pH adjustment) | Citric acid | 5 | 5 | 5 | 5 | 5 | 5 | 7 | 7 | 7 | 7 | 7 |

TABLE 2-continued

|  | Compositions with fillers of Examples | | | | | | | | | Compositions with fillers of Comparative Examples | |
|---|---|---|---|---|---|---|---|---|---|---|---|
|  | Composition 1 | Composition 2 | Composition 3 | Composition 4 | Composition 5 | Composition 6 | Composition 7 | Composition 8 | Composition 9 | Composition 10 | Composition 11 |
| powder/liquid (mass ratio) | 3.1 | 3.1 | 3.4 | 3.1 | 3.1 | 3.1 | 3.2 | 3.3 | 3.3 | 3.4 | 3.4 |
| Bending strength [Mpa] | 35.1 | 38.3 | 43.4 | 45.0 | 50.1 | 45.0 | 33.2 | 34.8 | 30.6 | 32.2 | 28.9 |

<<Making of Paste Type Dental Glass Ionomer Cement Composition>>

Each component was mixed at the blending amount shown in Table 3, whereby first pastes and second pastes of paste type dental glass ionomer cement compositions were prepared.

<<Pressure Resistance Strength Test>>

The first and second pastes prepared above were scaled at the paste ratios shown in Table 3, and kneaded for 10 seconds on a kneading paper by a spatula. A metal split mold of 4 mm in diameter and 6 mm in height was filled with the obtained kneaded material. The bottom and top of the mold were covered up by metal plates. With a clamp, the kneaded material with the mold was welded by pressure and fixed.

The obtained material was left in an atmosphere at a temperature of 37° C. and at a humidity of 100% for 1 hour to be cured. After that, the metal split mold was removed from the material. The obtained cylindrical specimen was immersed in 37° C. of water for 24 hours. Thereafter, the specimen was subjected to a compression test under a condition of 1 mm/min of crosshead speed, by a universal testing machine (Autograph, manufactured by Shimadzu Corporation). In each of the compositions 12 to 19, any one of the fillers for dental glass ionomer cements according to Examples 2 to 5, 7 and 8 was blended, and in each of the compositions 20 to 23, any one of the fillers according to Comparative Examples 1 to 3 was blended. The results are together shown in Table 3.

TABLE 3

|  |  |  | Compositions with fillers of Examples | | | | | | | |
|---|---|---|---|---|---|---|---|---|---|---|
|  |  |  | Composition 12 | Composition 13 | Composition 14 | Composition 15 | Composition 16 | Composition 17 | Composition 18 | Composition 19 |
| First paste | α-β unsaturated carboxylic acid polymer | Polyacrylic acid | 40 | 35 | 35 | 37 | 40 | 40 | 40 | 40 |
|  |  | Water | 40 | 35 | 40 | 38 | 45 | 40 | 45 | 40 |
|  | Filler for dental ionomer cement composition | Example 2 | 20 | 30 |  |  |  |  |  |  |
|  |  | Example 3 |  |  | 25 | 25 |  |  |  |  |
|  |  | Example 4 |  |  |  |  | 15 | 20 |  |  |
|  |  | Example 5 |  |  |  |  |  |  | 15 | 20 |
|  | Other filler | Comparative Example 1 |  |  |  |  |  |  |  |  |
|  |  | Comparative Example 2 |  |  |  |  |  |  |  |  |
|  |  | Comparative Example 3 |  |  |  |  |  |  |  |  |
| Second paste | Fluoroaluminosilicate glass powder | Fluoroaluminosilicate glass powder A | 75 | 75 | 70 | 70 | 71 | 71 |  |  |
|  |  | Fluoroaluminosilicate glass powder B |  |  |  |  |  |  | 50 | 50 |
|  |  | Water | 20 | 21 | 25 | 20 | 25 | 21 | 35 | 37 |
|  |  | Glycerin | 4.5 | 3.5 | 4.5 | 9.5 | 3.6 | 7.6 | 4.8 | 2.8 |
|  | Filler for dental ionomer cement composition | Example 7 |  |  |  |  |  |  | 10 |  |
|  |  | Example 8 |  |  |  |  |  |  |  | 10 |
|  | Viscosity improver | Sodium carboxymethylcellulose | 0.1 | 0.1 | 0.1 | 0.1 |  |  |  |  |
|  |  | Fine particle silica | 0.4 | 0.4 | 0.4 | 0.4 | 0.4 | 0.4 | 0.2 | 0.2 |
|  | first paste/second paste (mass ratio) |  | 0.8 | 0.8 | 0.8 | 0.8 | 0.8 | 0.8 | 1 | 1 |
|  | Pressure resistance strength [Mpa] |  | 45.1 | 48.1 | 59.7 | 60.3 | 56.3 | 58.1 | 55.6 | 53.1 |

|  |  |  | Compositions with fillers of Comparative Examples | | | |
|---|---|---|---|---|---|---|
|  |  |  | Composition 20 | Composition 21 | Composition 22 | Composition 23 |
| First paste | α-β unsaturated carboxylic acid polymer | Polyacrylic acid | 40 | 35 | 40 | 40 |
|  |  | Water | 45 | 40 | 45 | 45 |
|  | Filler for dental ionomer cement composition | Example 2 |  |  |  |  |
|  |  | Example 3 |  |  |  |  |
|  |  | Example 4 |  |  |  |  |
|  |  | Example 5 |  |  |  |  |

TABLE 3-continued

| | | | | | | |
|---|---|---|---|---|---|---|
| | Other filler | Comparative Example 1 | 15 | 25 | | |
| | | Comparative Example 2 | | | 15 | |
| | | Comparative Example 3 | | | | 15 |
| Second paste | Fluoroaluminosilicate glass powder | Fluoroaluminosilicate glass powder A | 64 | 64 | 64 | 64 |
| | | Fluoroaluminosilicate glass powder B | | | | |
| | | Water | 31 | 30 | 33 | 33 |
| | | Glycerin | 3.8 | 4.8 | 2.8 | 2.8 |
| | Filler for dental ionomer cement composition | Example 7 | | | | |
| | | Example 8 | | | | |
| | Viscosity improver | Sodium carboxymethylcellulose | 1 | 1 | | |
| | | Fine particle silica | 0.2 | 0.2 | 0.2 | 0.2 |
| | first paste/second paste (mass ratio) | | 1 | 1 | 1 | 1 |
| | Pressure resistance strength [Mpa] | | 40.5 | 42.1 | 39.1 | 41.5 |

From the results shown in Tables 2 and 3, it can be figured out that the filler for dental glass ionomer cements according to the present invention provided a higher strength to the hardened cement, in both cases where the filler was blended in a powder-liquid type composition and where the filler was blended in a paste type composition, compared to cases where the fillers of Comparative Examples were blended.

The invention claimed is:

1. A method for manufacturing a filler for dental glass ionomer cements comprising, in the order mentioned:
   treating a surface of an inorganic powder with a silane coupling agent having an unsaturated double bond(s), and
   binding a carboxylic acid having an unsaturated double bond(s) exclusive of a (meth)acrylate compound, to the inorganic powder whose surface is treated with the silane coupling agent.

2. The method for manufacturing a filler for dental glass ionomer cements according to claim 1, wherein the carboxylic acid having an unsaturated double bond(s) exclusive of a (meth)acrylate compound is one or two or more kinds selected from the group consisting of acrylic acid, methacrylic acid, itaconic acid, fumaric acid, maleic acid, aconitic acid, angelic acid, citraconic acid, crotonic acid, glutaconic acid, metaconic acid, mesaconic acid, muconic acid, tiglic acid, cinnamic acid, allylmalonic acid, butenoic acid, pentenoic acid, hexenoic acid, octenoic acid, nonenoic acid, decenoic acid, oleic acid, linoleic acid, and linolenic acid.

3. The method for manufacturing a filler for dental glass ionomer cements according to claim 1, wherein the binding is carried out in a dispersion medium.

4. The method for manufacturing a filler for dental glass ionomer cements according to claim 1, wherein the inorganic powder does not react with an acid in the presence of water.

5. The method for manufacturing a filler for dental glass ionomer cements according to claim 3, wherein the inorganic powder reacts with an acid in the presence of water, and the dispersion medium does not include water.

6. The method for manufacturing a filler for dental glass ionomer cements according to the claim 1, wherein a polymerization initiator is used in the binding.

7. The method for manufacturing a filler for dental glass ionomer cements according to the claim 6, wherein a blending amount of the polymerization initiator is in the range of from 0.1 to 3 mass % to the total amount of the inorganic powder treated with the silane coupling agent, the carboxylic acid, and the polymerization initiator.

8. The method for manufacturing a filler for dental glass ionomer cements according to the claim 6, wherein the polymerization initiator is a thermal polymerization initiator.

* * * * *